US007041832B2

(12) United States Patent
Dolitzky

(10) Patent No.: US 7,041,832 B2
(45) Date of Patent: May 9, 2006

(54) PROCESSES FOR PREPARING LOSARTAN AND LOSARTAN POTASSIUM

(75) Inventor: Ben-Zion Dolitzky, Petach Tiqva (IL)

(73) Assignee: Tava Pharmaceutical Industries, Ltd., Petach Tiqva (IL)

( * ) Notice: Subject to any disclaimer, the term of this patent is extended or adjusted under 35 U.S.C. 154(b) by 0 days.

(21) Appl. No.: 10/426,612

(22) Filed: Apr. 29, 2003

(65) Prior Publication Data
US 2004/0034077 A1    Feb. 19, 2004

Related U.S. Application Data

(60) Provisional application No. 60/376,322, filed on Apr. 29, 2002.

(51) Int. Cl.
*C07D 257/00*    (2006.01)
(52) U.S. Cl. .................. 548/252; 548/250; 548/254
(58) Field of Classification Search .............. 540/252, 540/250, 254
See application file for complete search history.

(56) References Cited

U.S. PATENT DOCUMENTS

| | | | |
|---|---|---|---|
| 4,340,598 | A | 7/1982 | Furukawa et al. |
| 4,355,040 | A | 10/1982 | Furukawa et al. |
| 5,002,953 | A | 3/1991 | Hindley |
| 5,128,355 | A | 7/1992 | Carini et al. |
| 5,130,439 | A * | 7/1992 | Lo et al. ..................... 548/110 |
| 5,138,069 | A | 8/1992 | Carini et al. |
| 5,155,118 | A | 10/1992 | Carini et al. |
| 5,155,188 | A | 10/1992 | Goodall |
| 5,206,374 | A | 4/1993 | Lo |
| 5,210,079 | A | 5/1993 | Carini et al. |
| 5,294,716 | A | 3/1994 | Thomas et al. |
| 5,310,928 | A * | 5/1994 | Lo et al. ..................... 548/252 |
| 5,332,744 | A | 7/1994 | Chakravarty et al. |
| 5,354,867 | A | 10/1994 | Carini et al. |
| 5,420,292 | A | 5/1995 | Thomas et al. |
| 5,484,955 | A | 1/1996 | Kato et al. |
| 5,599,943 | A | 2/1997 | Kato et al. |
| 5,608,075 | A | 3/1997 | Campbell, Jr. et al. |
| 5,663,186 | A | 9/1997 | Nelson et al. |
| 5,663,187 | A | 9/1997 | Nelson et al. |
| 5,952,509 | A | 9/1999 | Saito et al. |
| 5,962,500 | A | 10/1999 | Eide et al. |
| 6,350,880 | B1 | 2/2002 | Katsura et al. |
| 6,710,183 | B1 * | 3/2004 | Fischer et al. .............. 548/252 |
| 2002/0115702 | A1 | 8/2002 | Remuzzi |

FOREIGN PATENT DOCUMENTS

| | | |
|---|---|---|
| EP | 0 470 795 B2 | 8/1991 |
| EP | 0 470 494 A1 | 2/1992 |
| WO | 99/16437 | 4/1999 |
| WO | WO 02/080910 | 10/2002 |

OTHER PUBLICATIONS

Bradbury et al., "New Nonpeptide Angiotensin II Receptor Antagonists. 3.[1] Synthesis, Biological Properties, and Structure-Activity Relationships of 2-Alkyl-4-(biphenylylmethoxy) pyridine Derivatives", *Journal of Medicinal Chemistry* 1993, 36:9, pp. 1245-1254.
Carini et al. "Nonpeptide Angiotensin II Receptor Antagonists: The Discovery of a Seris of N-(Biphenylylmethyl_imidazoles as Potent, Orally Active Antihypertensives"*Journal of Medicinal Chemistry* 1991, 34:8 pp. 2525-2547.
Duncia et al., "Dibenzobicyclo [2.2.2.] octane angiotensin II Receptor Antagonists", *Bioorganic & Medicinal Chemistry Letters* 1995, 5:3, pp. 241-246.
Gibson et al., "New Triarylmethyl Derivatives: 'Blocking Groups' for Totaxanes and Polyrotaxanes", *J. Org. Chem.* 1993, 58:14, pp. 3748-3756.
Jinyi et al., "Synthesis of a New Type of Antihypertensive Agent Losartan", *Chinese Journal of Medicinal Chemistry* 1988, 8:4, pp. 271-276.
Joel R. Huff, "HIV Protease: A Novel Chemotherapeutic Target for AIDS", *Journal of Medicinal Chemistry* 1991, 34:8 2524-2547.
Kim et al., "Quinoxaline N-Oxide Containing Potent Angioensin II Receptor Antagonists: Synthesis, Biological Properties, and Structure-Activity Relationships", J. Med. Chem 1993, 36, pp. 2335-2342.
Larsen et al., "Efficient Synthesis of Losartan, A Nonpeptide Angiotensin II Receptor Antagonist", J. Org. Chem. 1994, 59, pp. 6391-6394.
Lo et al., "η-Butyl-2-(2'triphenylmethyltetrazol-50yl) phenylborinic Acid", *Journal of Heterocyclic Chemistry* 1995 32:1, pp. 355-357.
Marvel et al., "Alkyl Substituted Hexaarylethanes. XI.[1] Symmentry and Steric Effects as Factors in Dissociation", *J. Am. Chem. Soc.* 1941, 63, pp. 1892-1896.

(Continued)

*Primary Examiner*—Taofiq Solola
*Assistant Examiner*—Robert Shiao
(74) *Attorney, Agent, or Firm*—Kenyon &Kenyon LLP

(57) ABSTRACT

Losartan is prepared by acid catalyzed cleavage of a triarylmethyl group from a triarylmethyl-substituted losartan derivative in a diluent comprising liquid ketone. The reaction mixture is basified and liquid ketone is evaporated from the mixture leaving a residue from which a triarylmethyl alcohol and losartan are each obtained in high yield and high purity. In addition, losartan potassium is prepared by a process that is more convenient that those previously known in the art in which losartan is contacted with potassium ions in substantially pure liquid alcohol and losartan potassium is precipitated from the alcohol.

27 Claims, No Drawings

OTHER PUBLICATIONS

Nicolaï et al., "Synthesis and angiotensin II receptor antagonist activity of C-linked pyrimidine derivatives", *Eur. J. Med. Chem.* 1995, 30, pp. 365-375.

Pettit et al., "The Dolastatins. 21. Synthesis, X-ray Crystal Structure, and Molecular Modeling of (6R)-Isodolastatin 10[1a]", *The Journal of Organic Chemistry* 1994 59:21 6390-6394.

Sharma et al., "Enzymatic Lactonization Stategy for Enantioselective Synthesis of a Tetrahydrolipstatin Synthon", *J. Org. Chem.* 1999, 64:22, pp. 8083-8089.

Wang et al., "Synthesis of Novel Isoxazole-contained Analogues of Losartan", *Chinese Chemical Letters* 2000, 11:11, pp. 961-962.

Zhongguo Yaowu Huaxuie Zazhi, *Chinese Journal of Medicinal Chemistry* 1998, 8:4 271-276.

\* cited by examiner

PROCESSES FOR PREPARING LOSARTAN AND LOSARTAN POTASSIUM

CROSS-REFERENCE TO RELATED APPLICATION

This application claims the benefit under 35 U.S.C. §119 (e) of provisional application Ser. No. 60/376,322, filed Apr. 29, 2002 which is incorporated herein by reference.

FIELD OF THE INVENTION

The present invention relates to therapeutic agents that inhibit angiotensin II binding to $AT_1$ receptors and, more particularly, to a process for preparing the $AT_1$ receptor antagonist losartan.

BACKGROUND OF THE INVENTION

Activation of $AT_1$ receptors in the outer membrane of vascular smooth muscle cells of the heart and arteries causes those tissues to constrict. Blocking of vasoconstriction mediated by $AT_1$ receptors has been found to be beneficial to patients with hypertension.

$AT_1$ receptors are activated by an octa-peptide, angiotensin II. Angiotensin II helps to maintain constant blood pressure despite fluctuations in a person's state of hydration, sodium intake and other physiological variables. Angiotensin II also performs the regulatory tasks of inhibiting excretion of sodium by the kidneys, inhibiting norephedrin reuptake and stimulating aldosterone biosynthesis.

Inhibiting angiotensin II binding to $AT_1$ receptors with an $AT_1$ receptor antagonist disrupts the vasoconstriction mediated by $AT_1$ receptors that contributes to hypertension.

In the early 1970s, it was discovered that certain oligopeptides competitively inhibited angiotensin receptors (at that time the existence of two receptor subtypes, $AT_1$ and $AT_2$, was unknown). This discovery spurred interest in development of therapeutic oligopeptides with increased potency, but interest in peptide analogs waned due in part to their poor oral bioavailability.

In 1982, Furukawa, Kishimoto and Nishikawa of Taketa Chemical Indus. discovered a class of non-peptide-containing imidazoles that also inhibited the vasoconstriction effect of angiotensin II. See U.S. Pat. Nos. 4,340,598 and 4,355,040. Later, U.S. Pat. No. 5,138,069 was obtained by Carini, Denucia and Pancras of E. I. DuPont de Nemours on another class of imidazoles, which encompasses the compound losartan. In 1995, losartan (CA Index: 2-butyl-4-chloro-1-[[2'-(1H-tetrazol-5-yl) [1,1'-biphenyl]-4-yl]methyl]-1H-imidazole-5-methanol) (formula I):

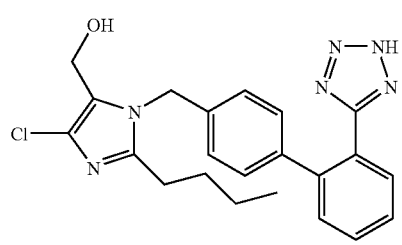

(I)

became the first nonpeptide $AT_1$ antagonist approved by the U.S. Food and Drug Administration for clinical use. Losartan can be administered orally as its mono-potassium salt. Losartan potassium is available by prescription in tablet form as a sole active ingredient (Cozaar®: Merck) and as a co-active ingredient with hydrochlorothiazide (Hyzaar®: Merck).

Losartan has been prepared by a variety of synthetic pathways. In several of these synthetic pathways, the penultimate product is 2-butyl-4-chloro-1-[[2'-(2-triphenylmethyl-2H-tetrazol-5-yl) [1,1'-biphenyl]-4-yl]methyl]-1H-imidazole-5-methanol ("trityl losartan"). Trityl losartan is an intermediate in processes described in U.S. Pat. Nos. 5,138,069; 5,962,500 and 5,206,374.

In a process described in Example 316 of U.S. Pat. No. 5,138,069, the tetrazole ring of losartan is formed by reacting 1-[(2'-cyanobiphenyl-4-yl)methyl]-2-butyl-4-chloro-5-hydroxymethylimidazole with trimethyltin azide. The reaction gives a trimethylstannyl substituted tetrazole compound directly. The trimethylstannyl group is cleaved from the product by reacting with trityl chloride. This reaction results in attachment of the trityl group to the tetrazole ring. In the last step, the trityl group is cleaved with acid to give losartan (Scheme 1).

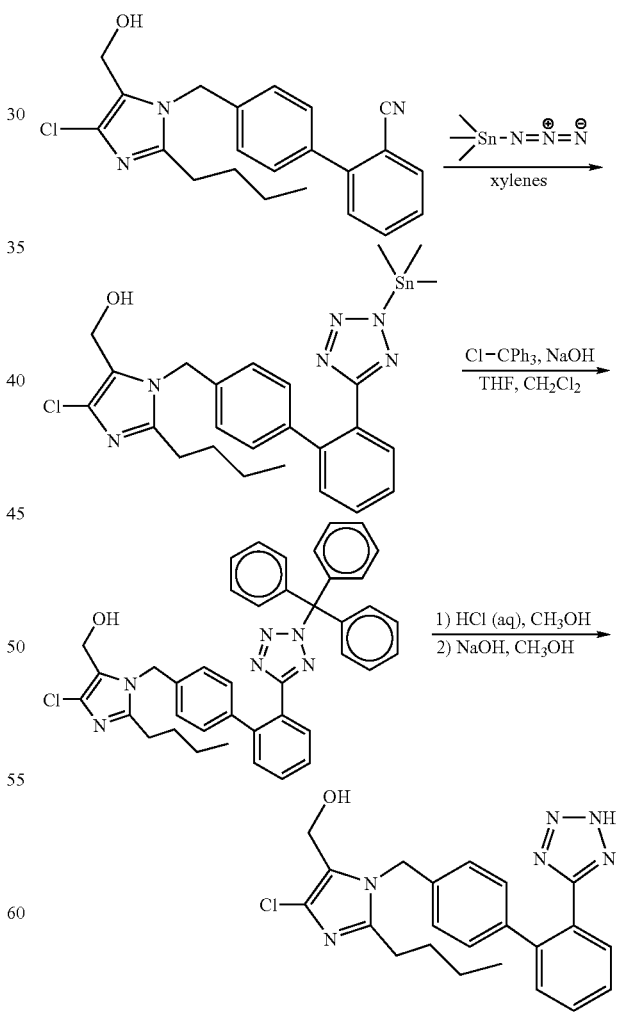

Scheme 1

In the last step, trityl losartan was suspended in methanol and cooled to ~10° C. 3.4 N Hydrochloric acid was added to the slurry. After a period of time, the pH of the reaction mixture was raised to 13 with 10 N NaOH. Methanol was then distilled off while makeup water was added. After distillation, additional water and toluene were added. The toluene phase was separated and the aqueous phase was extracted once more with toluene. Ethyl acetate and acetic acid were then added to the aqueous phase. Losartan was recovered from the aqueous phase as a solid and further purified by slurrying in ethyl acetate. Losartan was obtained in 88.5% yield and 98.8% purity as determined by HPLC. This process is also described in U.S. Pat. Nos. 5,128,355 and 5,155,188.

U.S. Pat. No. 5,962,500, Examples 3–5, describe a process for preparing losartan in which the tetrazole ring of losartan is present in the starting material, 5-phenyltetrazole.

The '500 patent process, depicted in Scheme 2, is convergent and uses a Suzuki coupling reaction (Miyaura, N.; Suzuki, A. *Chem. Rev.*, 1995, 95, 2457) in the convergent step. On one branch of the synthesis, 5-phenyltetrazole is converted into the boronic acid coupling partner for the Suzuki reaction by ortho metalation with n-butyl lithium, followed by reaction with trisopropylborate. The tetrazole ring is protected from reacting with the strong alkyl lithium base with a trityl group. The trityl group is conventionally attached by reacting the tetrazole with trityl chloride in the presence of a non-nucleophilic base. On the other branch of the convergent synthesis, 2-n-butyl-4-chloro-1H-imidazole-5-carboxaldehyde is alkylated with 4-bromobenzylbromide, followed by reduction of the aldehyde with sodium borohydride to yield the other Suzuki coupling partner.

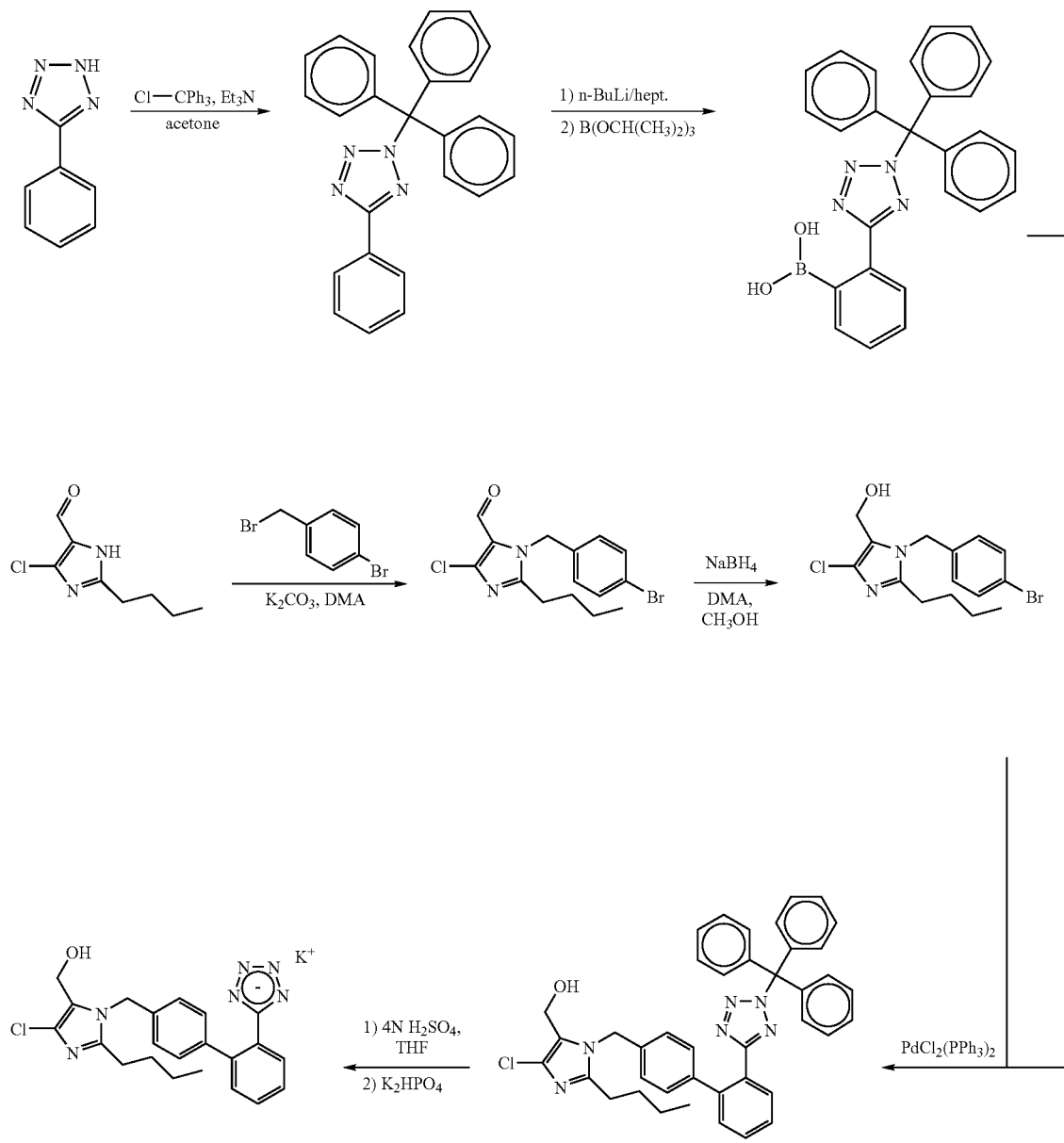

Scheme 2

The direct product of Suzuki coupling is trityl losartan. In the next and last step, the tetrazole ring of trityl losartan is deprotected with 4N H$_2$SO$_4$ in THF. In that step, the acidic solution was aged overnight at 20 to 25° C. The solution was then extracted with isopropyl acetate and residual organic solvent was removed from the aqueous phase under vacuum. The solution was then carried forward to form the potassium salt without intermediate isolation of losartan. This process is also described in U.S. Pat. Nos. 5,206,374, Example 21, and 5,310,928, Example 21.

U.S. Pat. No. 5,206,374 Examples 1 and 4–8 describe another process for making losartan that also involves a Suzuki coupling reaction. However, unlike the '500 patent process, the '374 patent process is not convergent. The '374 patent process is depicted in Scheme 3.

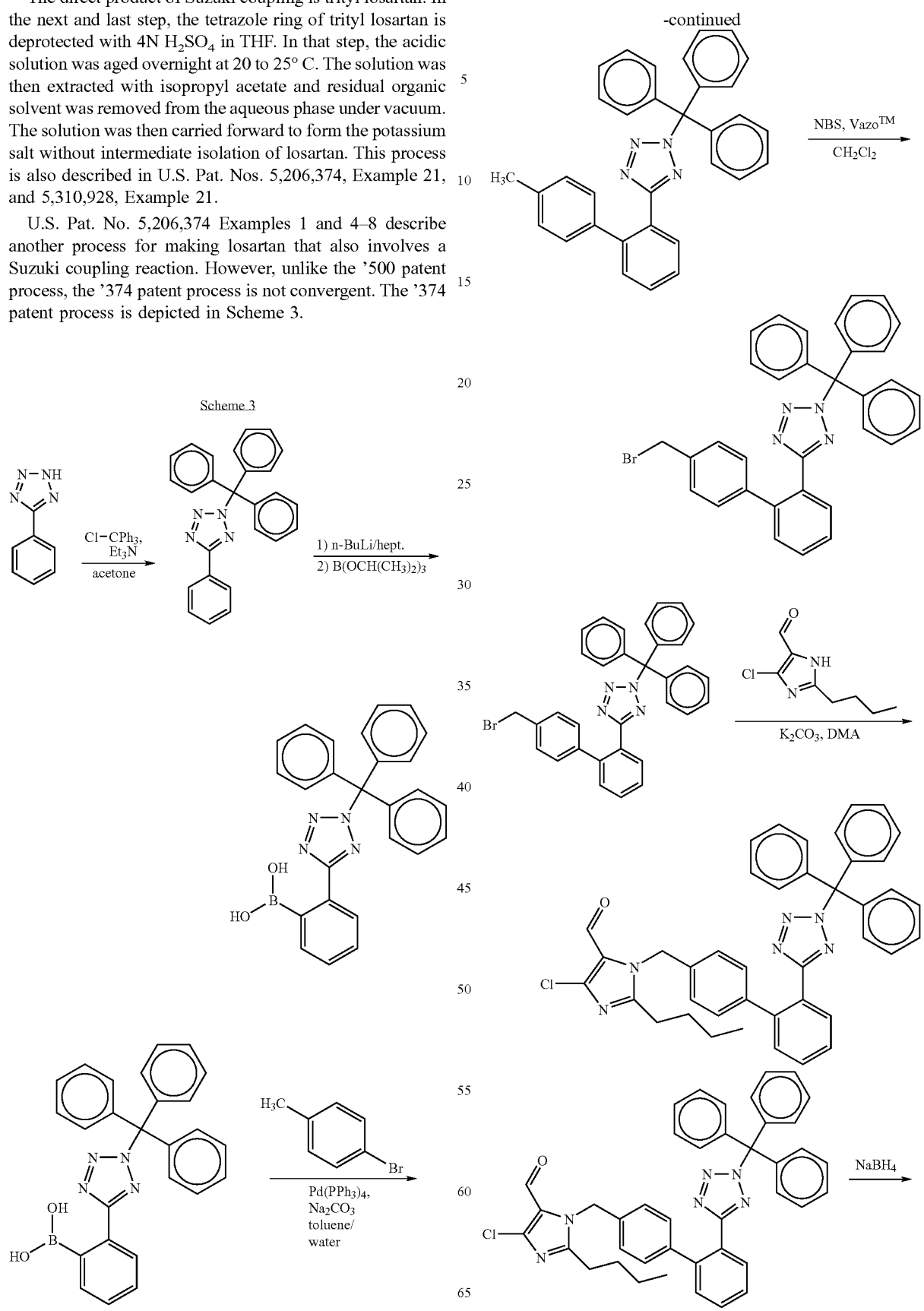

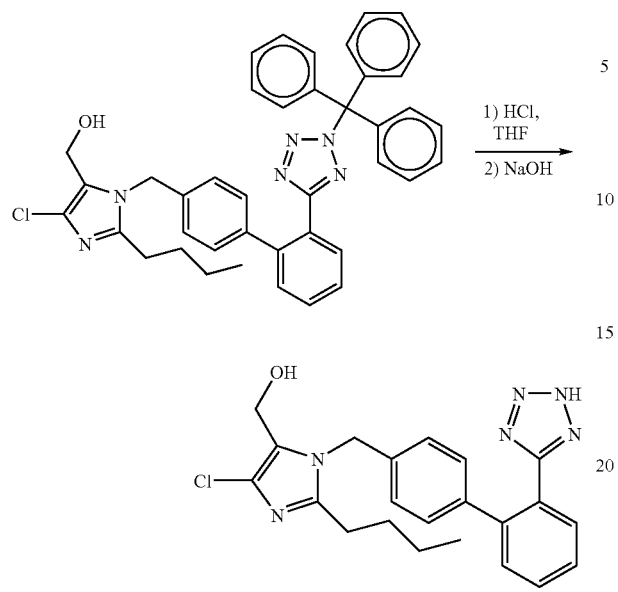

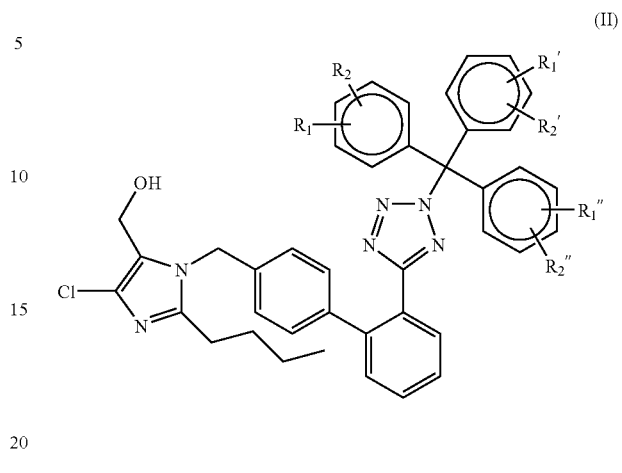

In the '374 patent process, as in the '500 patent process, the tetrazole ring of 5-phenyltetrazole is protected with a trityl group before orthometallation of the phenyl moiety with n-butyl lithium in preparation for making the boronic acid Suzuki coupling partner. In the Suzuki coupling step, the boronic acid is reacted with 4-bromotoluene. The methyl group attached to one of the phenyl rings of the Suzuki product is then halogenated with N-bromosuccinamide and the benzylic bromine atom of that product is displaced with 2-n-butyl-4-chloro-1H-imidazole-5-carboxaldehyde.

Reduction of the aldehyde group with sodium borohydride yields trityl losartan. The tetrazole group of trityl losartan was deprotected with 12% aqueous HCl in THF. After 12 hours, the pH of the reaction mixture was raised to 12.5 with 30% NaOH. The THF was then distilled off while make-up water was added to the mixture. After distillation, the mixture was cooled and the triphenyl methanol byproduct of deprotection, which had precipitated, was removed by filtration. The filtrate and rinsate, with which it was combined, were extracted with toluene. Then, ethyl acetate was added and 36% HCl was added until the pH of the reaction mixture was lowered to 3.8. The mixture was cooled, causing losartan to precipitate from the solution. Losartan was obtained in 83% theoretical yield starting from trityl losartan.

In view of the foregoing, it will be appreciated that trityl losartan is a significant intermediate compound in several synthetic pathways to the important therapeutic compound losartan. It would be highly desirable to have an improved process for preparing losartan from a triarylmethyl-substituted derivative of losartan, like trityl losartan.

SUMMARY OF THE INVENTION

In one aspect, the present invention provides a process for preparing losartan from a triarylmethyl-substituted derivative of losartan of formula (II):

wherein each $R_1$, $R_2$, $R_1'$, $R_2'$, $R_1''$ and $R_2''$ is independently selected from the group consisting of hydrogen; halogen; alkyl, which may be optionally substituted with one or more halogen, hydroxy or lower alkoxy; alkenyl, which may be optionally substituted with one or more halogen, hydroxy or lower alkoxy; nitro; cyano; vinyl; styryl; a group of formula —$COR_3$, —$CO_2R_3$, —$OR_3$, —$SR_3$, —$SO_2R_3$, —$NR_3R_4$, —$NCO_2R_3$, or —$OCO_2R_3$ where $R_3$ and $R_4$ are atoms and radicals independently selected from the group consisting of hydrogen, lower alkyl, aralkyl, aryl and heteroaryl; or where $R_1$ and $R_2$ occupy two adjacent positions they may be joined to form an optionally substituted carbocyclic or heterocyclic ring. In accordance with the process, the triarylmethyl-substituted derivative is contacted with an acid in a diluent comprising a liquid ketone for a period of time sufficient to substantially convert it into losartan. Thereafter, the diluent is basified and liquid ketone is evaporated leaving a residue. A triarylmethyl alcohol byproduct of the reaction is precipitated from the residue and removed. The residue is then acidified, which causes losartan to precipitate, whereupon it can be separated from the residue and obtained in high yield and purity.

In one embodiment of the process for preparing losartan, the triarylmethyl alcohol is converted into a reagent suitable for protecting a tetrazole group and then the reagent is used to prepare a compound of formula (II). In this way, the triarylmethyl moiety is recycled, rather than being disposed. Recycling is facilitated by the present invention because the triarylmethyl alcohol can be conveniently recovered by precipitation from the residue in high yield and high purity.

In another aspect, the present invention provides a process for preparing losartan potassium from losartan. According to the process, losartan is contacted with potassium in an isopropyl alcohol solvent and thereafter losartan potassium is precipitated from the solvent. This process yields losartan potassium in high yield and purity without cumbersome procedures required in prior art processes.

In yet another aspect, the present invention provides losartan and losartan potassium prepared by the processes of the present invention and pharmaceutical compositions containing losartan and losartan potassium prepared by one or more of the processes of the present invention.

DETAILED DESCRIPTION OF THE PREFERRED EMBODIMENTS

The present invention provides a process for preparing losartan from a triarylmethyl-substituted derivative of losartan of formula (II):

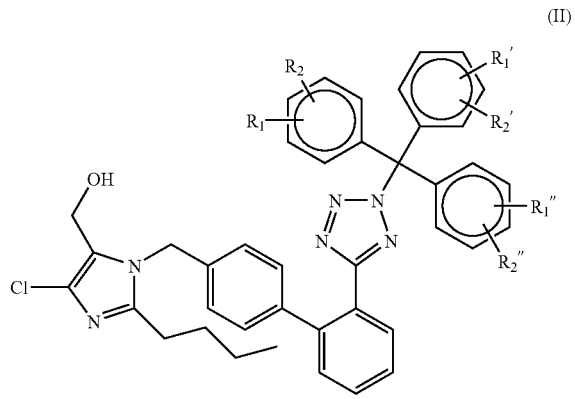

(II)

wherein each $R_1$, $R_2$, $R_1'$, $R_2'$, $R_1''$ and $R_2''$ is independently selected from the group consisting of hydrogen; halogen; alkyl, which may be optionally substituted with one or more halogen, hydroxy or lower alkoxy; alkenyl, which may be optionally substituted with one or more halogen, hydroxy or lower alkoxy; nitro; cyano; vinyl; styryl; a group of formula —$COR_3$, —$CO_2R_3$, —$OR_3$, —$SR_3$, —$SO_2R_3$, —$NR_3R_4$, —$NCO_2R_3$, or —$OCO_2R_3$ where $R_3$ and $R_4$ are atoms and radicals independently selected from the group consisting of hydrogen, lower alkyl, aralkyl, aryl and heteroaryl; or where $R_1$ and $R_2$ occupy two adjacent positions they may be joined to form an optionally substituted carbocyclic or heterocyclic ring, In preferred compounds of the present invention, each $R_1$, $R_2$, $R_1'$, $R_2'$, $R_1''$ and $R_2''$ is independently selected from the group consisting of hydrogen and methoxy or, when $R_1$ and $R_2$ or $R_1'$ and $R_2'$ or $R_1''$ and $R_2''$ occupy adjacent positions then the combination of $R_1$ and $R_2$ or $R_1'$ and $R_2'$ or $R_1''$ and $R_2''$ can be —CHCHCHCH—.

According to the process of the present invention, the triarylmethyl-substituted losartan of formula (II) is converted to losartan with an acid in a diluent comprising a liquid ketone and losartan is recovered from the diluent. Cleavage of a triarylmethyl group from a substrate molecule of formula (II) by this process produces a triarylmethyl alcohol of formula (III)

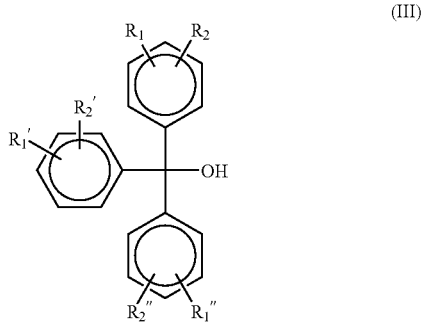

(III)

as a byproduct. The process of the present invention includes means for separating the triarylmethyl alcohol from losartan.

Triarylmethyl-substituted losartan of formula (II) can be prepared by following procedures described in U.S. Pat. Nos. 5,138,069, 5,206,374 and 5,962,500, which are hereby incorporated by reference in their entirety and, in particular, for their teachings relating to preparation of trityl losartan. In addition, these processes can be made to yield other triarylmethyl-substituted losartan compounds that are suitable starting materials for the process of the present invention by using appropriately substituted triarylmethyl chlorides and triarylmethyl tetrafluoroborates in place of the triphenylmethylchloride used in the examples of those patents. For instance, one method of preparing a triarylmethyl-substituted losartan derivative of formula (II) involves:

a) protecting 5-phenyltetrazole with a triarylmethyl reagent suitable for protecting a tetrazole under conditions effective to produce a 2-(triarylmethyl)-5-phenyltetrazole, b) converting the 2-(triarylmethyl)-5-phenyltetrazole to a 2-(2'-triarylmethyl-2'H-tetrazol-5'yl)phenylboronic acid compound, which can be done by orthometallating the phenyl ring with n-butyl lithium (or other alkyl lithium) and then contacting the ortholithiated intermediate with triisopropyl borate or other alkyl borate followed by an appropriate aqueous workup, c) converting the 2-(2'-triarylmethyl-2'H-tetrazol-5'yl)phenylboronic acid compound to a compound of formula (II) by:

i) contacting the 2-(2'-triaryl-ethyl-2'H-tetrazol-5'yl)phenylboronic acid compound with 2-n-butyl-4-chloro-5-hydroxymethyl-1-para-bromobenzyl-1H-imidazole under Suzuki conditions effective for preparing a 2-n-butyl-4-chloro- 1-[(2'-(2-triarylmethyl-2H-tetrazol-5-yl)-1,1'-biphenyl-4-yl)methyl]-1H-imidazole-5-carboxaldehyde compound, said effective conditions involving a palladium catalyst such as $PdCl_2(PPh_3)_2$ which can be prepared in situ from palladium tetrachoride and triphenylphosphine using methods known in the art and $Pd(PPh_3)_4$, ii) converting the resulting 2-n-butyl-4-chloro- 1-[(2'-(2-triarylmethyl-2H-tetrazol-5-yl)-1,1'-biphenyl-4-yl)methyl]-1H-imidazole-5-carboxaldehyde to a compound of formula (II) as defined in claim 1 with a reducing agent, such as sodium borohydride, lithium aluminum hydride and the like, with sodium borohydride being preferred.

Another method of preparing a triarylmethyl-substituted losartan derivative of formula (II) involves:

a) protecting 5-phenyltetrazole with a reagent suitable for protecting a tetrazole under conditions effective to produce a 2-(triarylmethyl)-5-phenyltetrazole, b) converting the 2-(triarylmethyl)-5-phenyltetrazole to a 2-(2'-triarylmethyl-2'H-tetrazol-5'yl)phenylboronic acid compound, which can be done by orthometallating the phenyl ring with n-butyl lithium (or other alkyl lithium) and then contacting the ortholithiated intermediate with triisopropyl borate or other alkyl borate followed by an appropriate aqueous workup, c) converting the 2-(2'-triarylmethyl-2'H-tetrazol-5'yl)phenylboronic acid compound to a compound of formula (II) by:

i) contacting the 2-(2'-triarylmethyl-2'H-tetrazol-5'yl)phenylboronic acid compound with para-bromotoluene under Suzuki conditions effective for preparing a 5-(4'-methyl-1,1'-biphenyl-2-yl)-2-triarylmethyl-2H-tetrazole compound, said effective conditions involving a palladium catalyst such as $PdCl_2(PPh_3)_2$ which can be prepared in situ from palladium tetrachoride and triphenylphosphine using methods known in the art and Pd(PPh$_3$)$_4$, ii) contacting the 5-(4'-methyl-1,1'-biphenyl-2-yl)-2-triarylmethyl-2H-tetrazole compound with a brominating agent, such as N-bromosuccinimide under conditions effective to prepare a 5-(4'-bromomethyl-1,1'-biphenyl-2-yl)-2-triarylmethyl-2H-tetrazole compound, iii) contacting the 5-(4'-bromomethyl-1,1'-biphenyl-2-yl)-2-triarylmethyl-2H-tetrazole compound with 2-n-butyl-4-chloro-1H-imidazole-5-carboxaldehyde under displacement conditions effective to prepare a 2-n-butyl-4-chloro-1-[(2'-(2-triarylmethyl-2H-tetrazol-5-yl)-1,1'-biphenyl-4-yl)methyl]-1H-imidazole-5-carboxaldehyde compound, which displacement conditions typically include a non-nucleophilic base to scavenge the HBr byproduct of the reaction, iv) converting the 2-n-butyl-4-chloro-1-[(2'-(2-triarylmethyl-2H-tetrazol-5-yl)-1,1'-biphenyl-4-yl)methyl]-1H-imidazole-5-carboxaldehyde to a compound of formula (II) with a reducing agent such as sodium borohydride or lithium aluminum hydride, with sodium borohydride being preferred.

In accordance with the present invention, the triarylmethyl-substituted losartan is contacted with an acid in a diluent comprising a ketone that is liquid at room temperature. Preferred liquid ketones are those that either have a lower boiling point than water or azeotrope with water. Yet more preferred liquid ketones are those in which water is highly soluble. Especially preferred liquid ketones are acetone, methyl ethyl ketone, and methyl isobutyl ketone, with acetone being the most preferred.

Any acid that is soluble in the diluent can be used in any amount that will catalyze removal of the triarylmethyl group from losartan. Acids which have been found suitable include hydrochloric acid, sulfuric acid, acetic acid, trifluoroacetic acid, hydrobromic acid and formic acid. Hydrochloric acid and sulfuric acid are especially preferred. Preferably, monoprotic acids are added in an amount of from about 2 to about 4 equivalents with respect to the triarylmethyl-substituted losartan and diprotic acids are added in an amount of from about 1 to about 2 equivalents with respect to the triarylmethyl-substituted losartan.

The triarylmethyl-substituted losartan of formula (II), the acid, and the diluent may be combined in any order desired. Conveniently, the triarylmethyl-substituted losartan is first added to the liquid ketone, which may produce either a solution or suspension depending upon the amount of triarylmethyl-substituted losartan used. Then, an aqueous solution of the acid is preferably added. Thus, according to a preferred embodiment of the process for preparing losartan, the diluent is a mixture of a liquid ketone and water.

In the preferred embodiment wherein the process is conducted in a mixture of liquid ketone and water, the mixture preferably contains from about 10% to about 50% water and from about 50% to about 90% liquid ketone. When the acid and water are added concurrently as an aqueous acid, the normality of the acid can be predetermined to provide the appropriate amount of acid and water.

Depending upon the amount of triarylmethyl-substituted losartan that is added to the diluent, it will initially be either homogeneous or heterogeneous. After the triarylmethyl-substituted losartan has been substantially converted to losartan and the triarylmethyl alcohol, a clear or faintly cloudy solution should be obtained. The triarylmethyl-substituted losartan of formula (II) is preferably supplied in an amount sufficient to yield a solution that is from about 0.05 M to about 10 M in losartan calculated based upon complete conversion of the starting material. Completion of the reaction typically takes from about 3 to about 8 hours at room temperature. The extent of conversion can be monitored by thin layer chromatography (e.g. SiO$_2$, 50% EA/hex.) or other conventional means.

After the conversion has gone substantially to completion, the reaction mixture is basified. Preferred bases are alkali metal hydroxides and alkoxides such as sodium hydroxide, potassium hydroxide and sodium methoxide. Especially preferred bases are sodium hydroxide and potassium hydroxide, with potassium hydroxide being the most preferred. The base can be added neat, i.e. as a solid, or as an aqueous solution. The base is preferably added in an amount that raises the pH of the mixture to from about 10 to about 14. Addition of the base is understood to convert the losartan to a soluble alkali metal salt of losartan. The triarylmethyl alcohol is not substantially converted to an alkali metal triarylmethoxide.

After addition of the base, the liquid ketone is evaporated, which is preferably performed at ambient temperature under vacuum. Removal of the liquid ketone tends to selectively drive the un-ionized triarylmethyl alcohol out of solution. Thus, the residue initially is a mixture of solid triarylmethyl alcohol and a liquid. The liquid component of the residue may be monophasic or biphasic. The triarylmethyl alcohol can then be separated from the residue by filtering, decanting, centrifuging or other conventional means. Further, it can be washed with water and the washings can be combined with the residue to further increase recovery of losartan. The triarylmethyl alcohol can be recovered in high yield and good purity (See example 1, where the % recovery is 91% and purity is 97.7%). The recovered triarylmethyl alcohol can then be converted to a reagent suitable for protecting tetrazole. Thus, in one embodiment of the process for preparing losartan of the present invention involves recycling of the triarylmethyl protecting group in a process for preparing losartan. Reagents suitable for protecting tetrazole include triarylmethyl chlorides or triarylmethyl tetrafluoroborates, which can be prepared from triarylmethyl alcohols by following methods well known in the art. For example, triarylmethyl alcohols can be converted to triarylmethylchlorides with acetyl choride as described in *J. Am. Chem. Soc.* 1941, 63, 1892; *J. Am. Chem. Soc.* 1986, 108, 3762; and *J. Org. Chem.* 1993, 58, 3748; with trimethylsilylchloride as described in *J. Org. Chem.* 1988, 53, 3634, and by using harsher conditions such as with HCl as described in *Org. Syn. Coll.* Vol. 1 1932, 286, 288, 519. All of the references cited in this paragraph are hereby incorporated by reference in their entirety.

After separating the triarylmethyl alcohol from the residue, there is an opportunity to remove nonpolar impurities from the product mixture by extracting the residue with a water immiscible organic solvent, such as ethyl acetate. The organic phase can be separated from the aqueous phase containing losartan before proceeding to the next step of the process or it may remain in contact with it in the next step of the process.

After separation of the triarylmethyl alcohol from the residue and optional extraction, the residue is acidified. Preferably, the residue is acidified to a pH of about 3 to about 4, more preferably about 3.5 to about 3.6. While any protic acid can be used, preferred acids are hydrochloric acid, sulfuric acid, acetic acid, trifluoroacetic acid, hydrobromic acid and formic acid. Hydrochloric acid and sulfuric acid are yet more preferred, with 3N hydrochloric acid and 66% aqueous sulfuric acid being especially preferred. Acidification of the residue liberates losartan from its alkali metal salt. Free losartan, being less polar than its alkali metal salt precipitates from the residue and can be separated from the water, residual acetone and other soluble components of the residue by filtering, decanting, centrifuging and the like.

If the organic phase is not separated from the aqueous phase before acidification, additional losartan can be recovered from it, e.g. by partial concentration of the organic phase and crystallization of losartan therefrom.

By practice of the present invention, losartan can be prepared from triarylmethyl-substituted losartan in high yield, e.g. 91 % and above, and in high purity, e.g. 97% and above.

The losartan obtained by the above-described process can be converted into its potassium salt by techniques known in the art, such as those described in U.S. Pat. Nos. 5,206,374, 5,138,069 and 5,962,500, which have previously been incorporated by reference and are hereby incorporated by reference for their disclosures related to formation of losartan potassium from losartan. Alternatively, losartan potassium can be prepared by the following novel process, which constitutes a second aspect of the invention.

Losartan is suspended in a diluent consisting essentially of an alcohol selected from the group consisting of isopropyl alcohol, butyl alcohol and isobutyl alcohol, preferably in an amount of from about 60 to about 100 grams of losartan per liter of diluent, more preferably in an amount of about 80 grams per liter. The preferred alcohol is isopropyl alcohol.

To the losartan suspension is added a solution of potassium ions in the diluent. The potassium ion solution may be prepared by a variety of techniques, including dissolving potassium isopropoxide, potassium butoxide, potassium isobutoxide or potassium hydroxide in the diluent. An amount of the potassium ion solution sufficient to deliver about one equivalent of potassium with respect to losartan, e.g. from 0.9 to 1.1 equivalents, is slowly added to the suspension. Over time, which is typically about 2 hours at room temperature, the losartan dissolves. Thereafter, the solution may be concentrated, preferably by about a third of its volume. If the concentrated solution is cloudy, then it can be heated to redissolve the losartan potassium until a clear solution is obtained. Upon allowing the solution to stand at room temperature or reduced temperature, losartan potassium will precipitate, whereupon it can be separated from the diluent by filtering, decanting and the like, and optionally washed and dried. By using a diluent of substantially pure alcohol to form the losartan potassium salt, the product is obtained conveniently in high yield and higher purity compared to the processes described in U.S. Pat. No. 5,138, 069, Example 316(D) and U.S. Pat. No. 5,206,374, Example 8. In those processes, a solution of losartan potassium in isopropanol is treated with a solution of potassium hydroxide in water. A substantial proportion of the water then has to be removed, e.g. by refluxing through a Dean-Stark trap, in order to be able to precipitate losartan potassium from the solution. Even then, an anti-solvent, heptane, has to be added to further reduce the polarity of the solvent. We have found that losartan can be converted to losartan potassium in substantially pure alcohols and that the losartan potassium can then be precipitated from the alcohol in high yield. Our process avoids the time-consuming process of distilling off water and having to add an anti-solvent in order to obtain losartan potassium in good yield. Although substantially pure alcohol should be used in our process, the alcohol does not need to be rigorously anhydrous or of especially high purity like spectrophotometric grade.

Losartan potassium prepared using one or more of the processes of the present invention is useful as an anti-hypertensive agent. For this purpose, it may be administered alone or in combination with other anti-hypertensive agents, such as diuretics like hydrochlorothiazide. Losartan potassium is effective when orally administered to adults in dosages ranging from 25 mg to 100 mg per day.

Losartan potassium prepared by one or more processes of this invention may be orally administered in a compressed tablet in which the losartan potassium is dispersed in a pharmaceutical vehicle. Pharmaceutical vehicles contain one or more excipients or adjuvants such as diluents, e.g. microcrystalline cellulose, lactose, hydroxypropylmethyl cellulose and the like; disintegrants, e.g. pregelatinized starch, croscarmellose sodium, crospovidone, sodium starch glycollate and the like; humectants e.g. triacetin, glycerol and the like; colorants, e.g. titanium dioxide, iron oxide yellow or iron oxide red; flavorings and the like.

Having thus described the present invention with reference to certain preferred embodiments, the processes for producing losartan and losartan potassium of the present invention are further illustrated by the examples which follow. These examples are provided for illustrative purposes only and are not intended to limit in any way the scope of the invention which is defined by the claims which follow the examples.

EXAMPLES

Example 1

Preparation of Losartan

Aqueous hydrochloric acid (3 N, 39.1 mL, 117.3 mmol, 3 eq.) was added to a suspension of trityl losartan (26.0 g, 39.1 mmol) in acetone (150 mL) at room temperature. The reaction mixture was stirred for about 5 hours.

A solution of potassium hydroxide (85%, 11.0 g, 195.5 mmol, 5 eq.) in water (100 mL) was slowly added and acetone was evaporated under reduced pressure. A slightly yellow precipitate was filtered, washed with water (2×20 mL), and dried under reduced pressure (about 10 mmHg) at about 50° C. Triphenyl methanol (10.1 g, 99% yield) was recovered in 94.6% purity as determined by HPLC.

Ethyl acetate (100 mL) was added to the aqueous filtrate and the biphasic mixture was vigorously stirred and acidified to pH 3.5–3.6 by slow addition of 3N hydrochloric acid (about 25 mL). The resulting suspension was stirred for an additional 30 minutes and filtered. The wet cake was washed with ethyl acetate (50 mL) and an acetone/water (50:50, 50 mL) mixture and dried under reduced pressure for about 2 hours at about 50° C. Losartan (15.0 g, 91.0% yield) was obtained in 97.68% purity as determined by HPLC.

Example 2

Preparation of Losartan

A 100 liter reactor was charged with water (7.4 kg), 66% aqueous sulfuric acid (2.235 kg), acetone (23.75 kg) and trityl losartan (5.0 kg). The mixture was stirred for 4 h and 20 min. at 25° C. A solution of potassium hydroxide (2.7 kg) in water (28.5 kg) was added to the stirred mixture over 30 minutes which raised the pH of the mixture to 13.3. The temperature of the mixture was maintained between 18 and 23° C. over the course of the addition. The mixture was stirred for 16 h at 20–25° C. and then concentrated to 47.2 kg under reduced pressued pressure (200 mbar) at 30–32° C. Precipitated triphenylmethanol was filtered off and washed while on the filter with water (2×5.0 kg).

The combined filtrate and rinsate were washed with ethyl acetate (13.5 kg) at 25° C. and the organic layer was separated. Fresh ethyl acetate (9.258 kg) was added to the aqueous layer and the two-phase mixture was acidified from pH 9.28 to 3.44 at 25° C. with 66% aqueous sulfuric acid (771 g). The resulting mixture was stirred for 12 hours at 25° C. and then filtered. The solids were washed with water (2×5.0 kg) at 25–30° C. and dried under reduced pressure at 40–50° C. to give losartan (2.864 kg, 90.1%) as white crystals. m.p.=180.5–181.7° C.

Example 3

Preparation of Losartan Potassium

A solution of potassium hydroxide (0.305 g, 4.62 mmol (1 eq.)) and isopropyl alcohol (15 mL) was slowly added to a suspension of losartan (2.0 g, 4.73 mmol) in isopropyl alcohol (25 mL). The reaction mixture was stirred for about 2 hours at room temperature. The mixture was filtered, concentrated to about a 15 mL volume, heated to reflux and stirred for about 12 hours at room temperature. The precipitate was filtered, washed with isopropyl alcohol (5 mL), and dried under reduced pressure for about 2 hours at about 50° C. to give losartan potassium (1.85 g, 85% yield) as a white powder. Purity was determined to be 99.74% by HPLC. Losartan potassium (1.0 g) was then triturated with ethyl acetate (10 mL) and recovered from the triturate in a purity of 99.775% by HPLC.

Example 4

Preparation of Losartan Potassium

A solution of potassium hydroxide (9.4 g) and isopropyl alcohol (200 mL) was slowly added to a suspension of losartan (60 g) in isopropyl alcohol (280mL). The reaction mixture was stirred for about 2 hours at room temperature. The mixture was filtered, heated to reflux, concentrated to about a 180 mL volume and stirred for about 12 hours at room temperature. The precipitate was filtered, washed with isopropyl alcohol, and dried under reduced pressure for about 2 hours at about 50° C. to give losartan potassium (52.2 g, 85% yield) as a white powder. Purity was determined to be 99.74% by HPLC. Losartan potassium (1.0 g) was triturated with ethyl acetate (10 mL) and recovered from the triturate in a purity of 99.775% by HPLC.

Having thus described the invention with respect to certain preferred embodiments and further illustrated it with examples, those skilled in the art may come to appreciate substitutions and equivalents that albeit not expressly described are taught and inspired by this invention. Whereas such substitutions and equivalents do not depart from the spirit of the invention they are within its scope which is defined by the claims that follow.

What is claimed is:
1. A process for preparing losartan of formula (I)

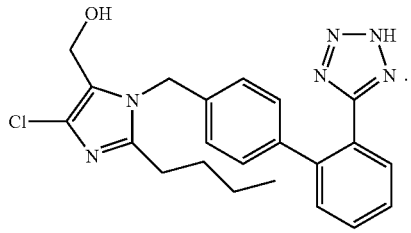
(I)

and pharmaceutically acceptable salts thereof comprising:
a) contacting a compound of formula (II):

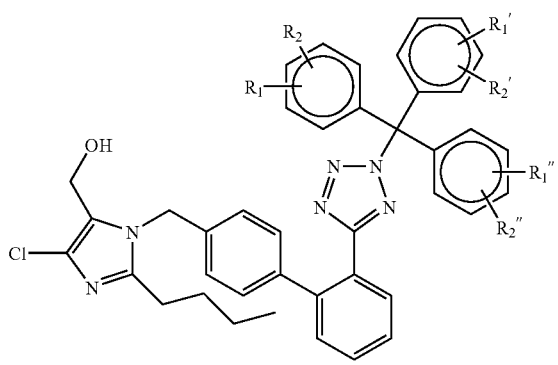
(II)

wherein each $R_1$, $R_2$, $R_1'$, $R_2'$, $R_1''$ and $R_2''$ is independently selected from the group consisting of hydrogen; halogen; alkyl, which may be optionally substituted with one or more halogen, hydroxy or lower alkoxy; alkenyl, which may be optionally substituted with one or more halogen, hydroxy or lower alkoxy; nitro; cyano; vinyl; styryl; a group of formula —$COR_3$, —$CO_2R_3$, —$OR_3$, —$SR_3$, —$SO_2R_3$, —$NR_3R_4$, —$NCO_2R_3$, or —$OCO_2R_3$ where $R_3$ and $R_4$ are atoms and radicals independently selected from the group consisting of hydrogen, lower alkyl, aralkyl, aryl and; or where $R_1$ and $R_2$ or $R_1'$ and $R_2'$ or $R_1''$ and $R_2''$ occupy two adjacent positions they may be joined to form an optionally substituted carbocyclic ring, and an acid in a diluent comprising a liquid ketone for a period of time sufficient to substantially convert the compound to losartan,
b) basifying the diluent,
c) evaporating liquid ketone, leaving a residue,
d) precipitating a triarylmethyl alcohol of formula (III):

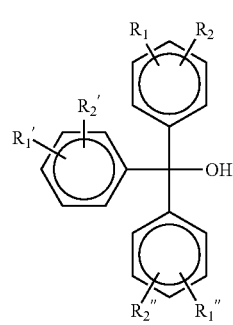
(III)

wherein $R_1$, $R_2$, $R_1'$, $R_2'$, $R_1''$ and $R_2''$ are as previously defined, from the residue,
e) separating the precipitated triarylmethyl alcohol from the residue,
f) acidifying the residue,
g) precipitating losartan from the residue, and
h) separating losartan from the residue.

2. The process of claim 1 wherein each $R_1$, $R_2$, $R_1'$, $R_2'$, $R_1''$ and $R_2''$ is independently selected from the group consisting of hydrogen and —$OCH_3$ or, where $R_1$ and $R_2$ or $R_1'$ and $R_2'$ or $R_1''$ and $R_2''$ occupy two adjacent positions, then the combination of $R_1$ and $R_2$ or $R_1'$ and $R_2'$ or $R_1''$ and $R_2''$ can be —CHCHCHCH—.

3. The process of claim 2 wherein the compound of formula (II) is selected from the group consisting of:
a) 2-butyl-4-chloro-1-[[2'-(2-triphenylmethyl-2H-tetrazol-5-yl) [1,1'-biphenyl]-4-yl]methyl]-1H-imidazole-5-methanol,
b) 2-butyl-4-chloro-1-[[2'-(2-(p-methoxyphenyl)diphenylmethyl-2H-tetrazol-5-yl) [1,1'-biphenyl]-4-yl]methyl]-1H-imidazole-5-methanol,
c) 2-butyl-4-chloro-1-[[2'-(2-di-(p-methoxyphenyl)phenylmethyl-2H-tetrazol-5-yl) [1,1'-biphenyl]-4-yl]methyl]-1H-imidazole-5-methanol,
d) 2-butyl-4-chloro-1-[[2'-(2-tri-(p-methoxyphenyl)methyl-2H-tetrazol-5-yl)[1,1'-biphenyl]-4-yl]methyl]-1H-imidazole-5-methanol,
e) 2-butyl-4-chloro-1-[[2'-(2-(p-methoxyphenyl-napth-1-yl-phenylmethyl)-2H-tetrazol-5-yl) [1,1'-biphenyl]-4-yl]methyl]-1H-imidazole-5-methanol,
f) 2-butyl-4-chloro-1-[[2'-(2-(p-methoxyphenyl-napth-2-yl-phenylmethyl)-2H-tetrazol-5-yl) [1,1'-biphenyl]-4-yl]methyl]-1H-imidazole-5-methanol,
g) 2-butyl-4-chloro-1-[[2'-(2-(di(p-methoxyphenyl)-napth-1-yl methyl)-2H-tetrazol-5-yl) [1,1'-biphenyl]-4-yl]methyl]-1H-imidazole-5-methanol.

4. The process of claim 3 wherein the compound of formula (II) is 2-butyl-4-chloro-1-[[2'-(2-triphenylmethyl-2H-tetrazol-5-yl) [1,1'-biphenyl]-4-yl]methyl]-1H-imidazole-5-methanol.

5. The process of claim 1 wherein the liquid ketone is selected from the group consisting of acetone, methyl ethyl ketone, and methyl isobutyl ketone.

6. The process of claim 5 wherein the liquid ketone is acetone.

7. The process of claim 1 wherein the diluent is a mixture of the liquid ketone and water.

8. The process of claim 7 wherein the mixture contains from about 10% to about 50% water and from about 50% to about 90% liquid ketone.

9. The process of claim 1 wherein the diluent is basified to a pH of from about 10 to about 14.

10. The process of claim 1 wherein the diluent is basified with a base selected from the group consisting of sodium hydroxide and potassium hydroxide.

11. The process of claim 10 wherein the base is potassium hydroxide.

12. The process of claim 1 further comprising:
i) converting the separated triarylmethyl alcohol to a triarylmethyl reagent suitable for protecting a tetrazole, and
j) using the triarylmethyl reagent to prepare a compound of formula (II) by reacting the triarylmethyl reagent with the tetrazole, resulting in a trityl group attached to the tetrazole.

13. The process of claim 12 wherein using the reagent comprises:
a) protecting 5-phenyltetrazole with the reagent to give a 2-(triarylmethyl)-5-phenyltetrazole,
b) converting the 2-(triarylmethyl)-5-phenyltetrazole to a 2-(2'-triarylmethyl-2'H-tetrazol-5'yl)phenylboronic acid compound,
c) converting the 2-(2'-triarylmethyl-2'H-tetrazol-5'yl)phenylboronic acid compound to a compound of formula (II), as defined in claim 1, by:
i) contacting the 2-(2'-triarylmethyl-2'H-tetrazol-5'yl) phenylboronic acid compound with 2-n-butyl-4-chloro-5-hydroxymethyl-1-para-bromobenzyl-1H-imidazole under Suzuki conditions effective for preparing a 2-n-butyl-4-chloro-1-[(2'-(2-triarylmethyl-2H-tetrazol-5-yl)-1,1'-biphenyl-4-yl)methyl]-1H-imidazole-5-carboxaldehyde compound,
ii) converting the 2-n-butyl-4-chloro-1-[(2'-(2-triarylmethyl-2H-tetrazol-5-yl)-1,1'-biphenyl-4-yl)methyl]-1H-imidazole-5-carboxaldehyde to a compound of formula (II) as defined in claim 1 with a reducing agent.

14. The process of claim 12 wherein using the reagent comprises:
a) protecting 5-phenyltetrazole with the reagent to give a 2-(triarylmethyl)-5-phenyltetrazole,
b) converting the 2-(triarylmethyl)-5-phenyltetrazole to a 2-(2'-triarylmethyl-2'H-tetrazol-5'yl)phenylboronic acid compound,
c) converting the 2-(2'-triarylmethyl-2'H-tetrazol-5'yl) phenylboronic acid compound to a compound of formula (II), as defined in claim 1, by:
i) contacting the 2-(2'-triarylmethyl-2'H-tetrazol-5'yl) phenylboronic acid compound with para-bromotoluene under Suzuki conditions effective for preparing a 5-(4'-methyl-1,1'-biphenyl-2-yl)-2-triarylmethyl-2H-tetrazole compound,
ii) contacting the 5-(4'-methyl-1,1'-biphenyl-2-yl)-2-triarylmethyl-2H-tetrazole compound with a brominating agent under conditions effective to prepare a 5-(4'-bromomethyl-1,1'-biphenyl-2-yl)-2-triarylmethyl-2H-tetrazole compound,
iii) contacting the 5-(4'-bromomethyl-1,1'-biphenyl-2-yl)-2-triarylmethyl-2H-tetrazole compound with 2-n-butyl-4-chloro-1H-imidazole-5-carboxaldehyde under conditions effective to prepare a 2-n-butyl-4-chloro-1-[(2'-(2-triarylmethyl-2H-tetrazol-5-yl)-1, 1'-biphenyl-4-yl)methyl]-1H-imidazole-5-carboxaldehyde compound, and
iv) converting the 2-n-butyl-4-chloro-1-[(2'-(2-triarylmethyl-2H-tetrazol-5-yl)-1,1'-biphenyl-4-yl)methyl]-1H-imidazole-5-carboxaldehyde to a compound of formula (II) as defined in claim 1 with a reducing agent.

15. The process of claim 1 wherein the residue is acidified to a pH of from about 2 to about 4.

16. The process of claim 15 wherein the residue is acidified to a pH of from about 3.5 to about 3.6.

17. The process of claim 1 wherein the residue is acidified with an acid selected from the group consisting of hydrochloric acid, sulfuric acid, acetic acid, trifluoroacetic acid, hydrobromic acid and formic acid.

18. The process of claim 17 wherein the acid is selected from the group consisting of hydrochloric acid and sulfuric acid.

19. The process of claim 1 further comprising extracting the residue with a water immiscible organic solvent after precipitating the triarylmethanol and before separating the losartan from the residue.

20. The process of claim 19 further comprising recovering losartan from the water immiscible organic solvent.

21. The process of claim 1 further comprising converting the losartan to losartan potassium.

22. The process of claim 21 wherein losartan is converted to losartan potassium by:
 a) contacting losartan with potassium in a diluent consisting essentially of an alcohol selected from the group consisting of isopropyl alcohol, butyl alcohol and isobutyl alcohol
 b) precipitating losartan potassium from the diluent and
 c) separating the precipitated losartan from the diluent.

23. The process of claim 22 wherein the alcohol is isopropyl alcohol.

24. The process of claim 22 wherein the losartan is contacted with an amount of potassium of from about 0.9 molar equivalents to about 1.1 molar equivalents with respect to the losartan.

25. The process of claim 23 further comprising evaporating a portion of the isopropyl alcohol diluent after contacting and before precipitating.

26. The process of claim 22 wherein losartan is contacted with potassium by adding a solution of potassium ions to a heterogeneous mixture of losartan and the diluent.

27. The process of claim 26 wherein the solution of potassium ions is prepared by adding a potassium ion source selected from the group consisting of potassium hydroxide, potassium isopropoxide, potassium butoxide and potassium isobutoxide to the diluent.

* * * * *

UNITED STATES PATENT AND TRADEMARK OFFICE
CERTIFICATE OF CORRECTION

PATENT NO. : 7,041,832 B2  Page 1 of 1
APPLICATION NO. : 10/426612
DATED : May 9, 2006
INVENTOR(S) : Gennady Nisnevich et al.

It is certified that error appears in the above-identified patent and that said Letters Patent is hereby corrected as shown below:

On Title Page # (75) Inventors, delete "Ben-Zion Dolitzky, Petach Tiqva (IL)"

On Title Page # (75) Inventors, insert --Gennady Nisnevich, Haifa (IL)--

On Title Page # (75) Inventors, insert --Igor Rukhman, Haifa, (IL)--

On Title Page # (75) Inventors, insert --Julia Kaftanov, Haifa, (IL)--

Signed and Sealed this

Seventh Day of November, 2006

JON W. DUDAS
*Director of the United States Patent and Trademark Office*